United States Patent
Ito

Patent Number: 5,618,339
Date of Patent: Apr. 8, 1997

[54] OSTEOINDUCTION SUBSTANCE, METHOD OF MANUFACTURING THE SAME, AND BONE FILLING MATERIAL INCLUDING THE SAME

[75] Inventor: Michio Ito, Nagano, Japan

[73] Assignee: Matsumoto Dental College, Nagano, Japan

[21] Appl. No.: 684,712

[22] Filed: Jul. 22, 1996

[30] Foreign Application Priority Data

Jul. 20, 1995 [JP] Japan ................... 7-183999

[51] Int. Cl.$^6$ .............. A61K 35/32; A61K 9/70
[52] U.S. Cl. .................. 106/124.3; 106/124.7; 424/549
[58] Field of Search ............ 106/124.3, 124.7, 106/135.1; 424/549

[56] References Cited

U.S. PATENT DOCUMENTS

| 4,394,370 | 7/1983 | Jefferies | 106/124.7 |
| 4,563,350 | 1/1986 | Nathan et al. | 106/124.7 |
| 4,627,982 | 12/1986 | Seyedin et al. | 106/124.7 |
| 5,001,169 | 3/1991 | Nathan et al. | 106/124.7 |

FOREIGN PATENT DOCUMENTS 6-24994  2/1994  Japan ................... A61K 33/10

OTHER PUBLICATIONS

Holtz, CA 121:238351 "The osteoinductive . . ." 1994.

*Primary Examiner*—David Brunsman
*Attorney, Agent, or Firm*—Foley & Lardner

[57] ABSTRACT

An osteoinduction substance is extracted from animal bones and essentially comprises Mg, Si, Ca, and Na. The osteoinduction substance is manufactured by subjecting the animal bone to acid dipping, liming, neutralization, thermal extraction, condensation, and dehydration to obtain gelatin. The gelatin is then subjected to deproteinization under a nonheat or a low-temperature condition to extract the osteoinduction substance. The osteoinduction substance is mixed with at least one of hydroxyapatite powder and chitosan to form a bone filling material. When the osteoinduction substance is mixed with chitosan sol, a bone filling material of a sheet type is obtained.

19 Claims, 2 Drawing Sheets

5,618,339

OSTEOINDUCTION SUBSTANCE, METHOD OF MANUFACTURING THE SAME, AND BONE FILLING MATERIAL INCLUDING THE SAME

BACKGROUND OF THE INVENTION

This invention relates to an osteoinduction substance for use mainly in dental treatment to accelerate creation of a new bone, to a method of manufacturing the osteoinduction substance, and to a bone filling material including the osteoinduction substance.

In dental treatment, attempts have been made of accelerating the reproduction of a bone by artificially implanting an osteoinduction substance in a resected site of a jaw bone.

In Japanese Unexamined Patent Publication No. 24994/1994, the present inventor proposes his earlier invention directed to such an osteoinduction substance which is extracted from animal bones and which contains $MgCO_3$, $Ca_2SiO_4$, CaO, and $Ca(OH)_2$.

The osteoinduction substance according to the above-mentioned earlier invention is artificially implanted in a resected site of a jaw bone to accelerate reproduction of a bone.

In the earlier invention, a small amount of the osteoinduction substance is mixed with chitosan sol and hydroxyapatite to form a bone filling material. The bone filling material can be formed not only into a hardenable type but also into a sheet type.

In order to manufacture the osteoinduction substance, the animal bones are at first dipped in acidic aqueous solution, rinsed, and subjected to liming. Then, the animal bones are again rinsed to remove water-soluble substances, keratin, and fat therefrom. As a consequence, a starting material is obtained. Subsequently, the starting material is neutralized by the use of acid, rinsed, and thereafter heated to obtain an extract. The extract is filtered to collect mother liquor. The mother liquor is subjected to vacuum condensation, cooled, and solidified into a solidified material. The solidified material is cut and dehydrated to obtain gelatin. The gelatin is heated at a high temperature into the osteoinduction substance. The osteoinduction substance thus obtained is effective in creation of a new bone when a small amount of the osteoinduction substance is added to apatite which is known as a bone filling material.

When the osteoinduction substance is mixed with chitosan sol, it is possible to manufacture the bone filling material of a sheet type containing the osteoinduction substance because the osteoinduction substance has an ability of gelatinizing the chitosan sol. It has also been confirmed that, by the use of the mixture of the osteoinduction substance and chitosan sol, the contents of CaO and ZnO can be reduced as compared with a neutral bone filling material of a hardenable type.

To obtain the osteoinduction substance, the gelatin is heated at a temperature between 600° C. and 1000° C. for one to two hours. During this high-temperature process, an offensive odor or malodor is inevitably emitted from the gelatin and brings about environmental pollution. In this connection, the osteoinduction substance must be manufactured by the use of a special heating apparatus capable of dealing with such offensive odor.

In addition, the gelatin is heated in a furnace to a high temperature ranging between 600° C. and 1000°C. Thus, the above-mentioned method is disadvantageous in view of heat economy.

SUMMARY OF THE INVENTION

It is therefore an object of this invention to provide an osteoinduction substance which is capable of effectively accelerating creation of a bone.

It is another object of this invention to provide a method of manufacturing an osteoinduction substance.

It is still another object of this invention to provide a bone filling material including an osteoinduction substance.

It is yet another object of this invention to provide a bone filling material of the type described, which can be processed into either a hardenable type or a sheet type so as to meet a wide range of applications.

According to an aspect of this invention, there is provided an osteoinduction substance which contains Mg, Si, Ca, and Na and which is prepared by the steps of subjecting animal bones to liming, neutralization, thermal extraction, condensation, and dehydration to obtain gelatin; and subjecting the gelatin to deproteinization which is carried out through a nonheat process or a low-temperature process.

In the above-mentioned osteoinduction substance, the deproteinization may be carried out by dissolving the gelatin in alkaline aqueous solution.

In the above-mentioned osteoinduction substance, NaOH aqueous solution is preferably used as the alkaline aqueous solution.

According to another aspect of this invention, there is provided a method of manufacturing an osteoinduction substance, comprising the steps of subjecting animal bones to acid dipping, liming, neutralization, thermal extraction, condensation, and dehydration to obtain gelatin; subjecting the gelatin to deproteinization which is carried out through a nonheat process or a low-temperature process; and filtering the solution to extract the osteoinduction substance.

In the above-mentioned method of manufacturing an osteoinduction substance, the deproteinization may be carried out by dissolving the gelatin in alkaline aqueous solution.

In the above-mentioned method of manufacturing an osteoinduction substance, NaOH aqueous solution is preferably used as the alkaline aqueous solution.

During the deproteinization, the NaOH aqueous solution may be heated at a low temperature between 80° C. and 85° C. for two to three hours.

According to still another aspect of this invention, there is provided a bone filling material comprising a mixture of an osteoinduction substance and at least one of hydroxyapatite powder and chitosan, the osteoinduction substance containing Mg, Si, Ca, and Na and manufactured by the steps of subjecting animal bones to liming, neutralization, thermal extraction, condensation, and dehydration to obtain gelatin, and subjecting the gelatin to deproteinization which is carried out through a nonheat process or a low-temperature process.

In the above-mentioned bone filling material, the deproteinization may be carried out by dissolving the gelatin in alkaline aqueous solution.

In the above-mentioned bone filling material, NaOH aqueous solution is used as the alkaline aqueous solution.

The above-mentioned bone filling material may include chitosan sol which is gelatinized by the osteoinduction substance to form the bone filling material into a sheet type.

In the above-mentioned bone filling material, the hydroxyapatite powder preferably has a particle size between 10 and 50 microns and includes at least one of crystallized hydroxyapatite powder and amorphous hydroxyapatite powder.

In the above-mentioned bone filling material, the hydroxyapatite powder is preferably composed of amorphous hydroxyapatite powder.

According to yet another aspect of this invention, there is provided a method of manufacturing a bone filling material, comprising the steps of preparing an osteoinduction substance by subjecting animal bones to acid dipping, liming, neutralization, thermal extraction, condensation, and dehydration to obtain gelatin, subjecting the gelatin to deproteinization which is carried out through a nonheat process or a low-temperature process, and filtering the solution to obtain the osteoinduction substance; and mixing the osteoinduction substance with at least one of hydroxyapatite powder and chitosan.

The above-mentioned method of manufacturing a bone filling material may comprise the steps of dissolving hydroxyapatite powder and chitosan by acid using physiological saline solution to form a sol material; and kneading the osteoinduction substance into the sol material to form paste as the bone filling material.

The above-mentioned method of manufacturing a bone filling material may further comprise the steps of dehydrating the paste by the use of liquid nitrogen, and shaping the paste into a sheet which serves as the bone filling material.

In the above-mentioned method of manufacturing a bone filling material, the deproteinization may be carried out by dissolving the gelatin in alkaline aqueous solution.

In the above-mentioned method of manufacturing a bone filling material, NaOH aqueous solution is used as the alkaline aqueous solution.

During the deproteinization, the NaOH aqueous solution may be heated at a low temperature between 80° C. and 85° C. for two to three hours.

DESCRIPTION OF THE PREFERRED EMBODIMENT

Prior to description of the present invention, a conventional osteoinduction substance and a conventional method of manufacturing the osteoinduction substance will at first be described.

As described in the foregoing, the present inventor already proposed an osteoinduction substance which is extracted from animal bones and which contains $MgCO_3$, $Ca_2SiO_4$, $CaO$, and $Ca(OH)_2$.

Figure 1:
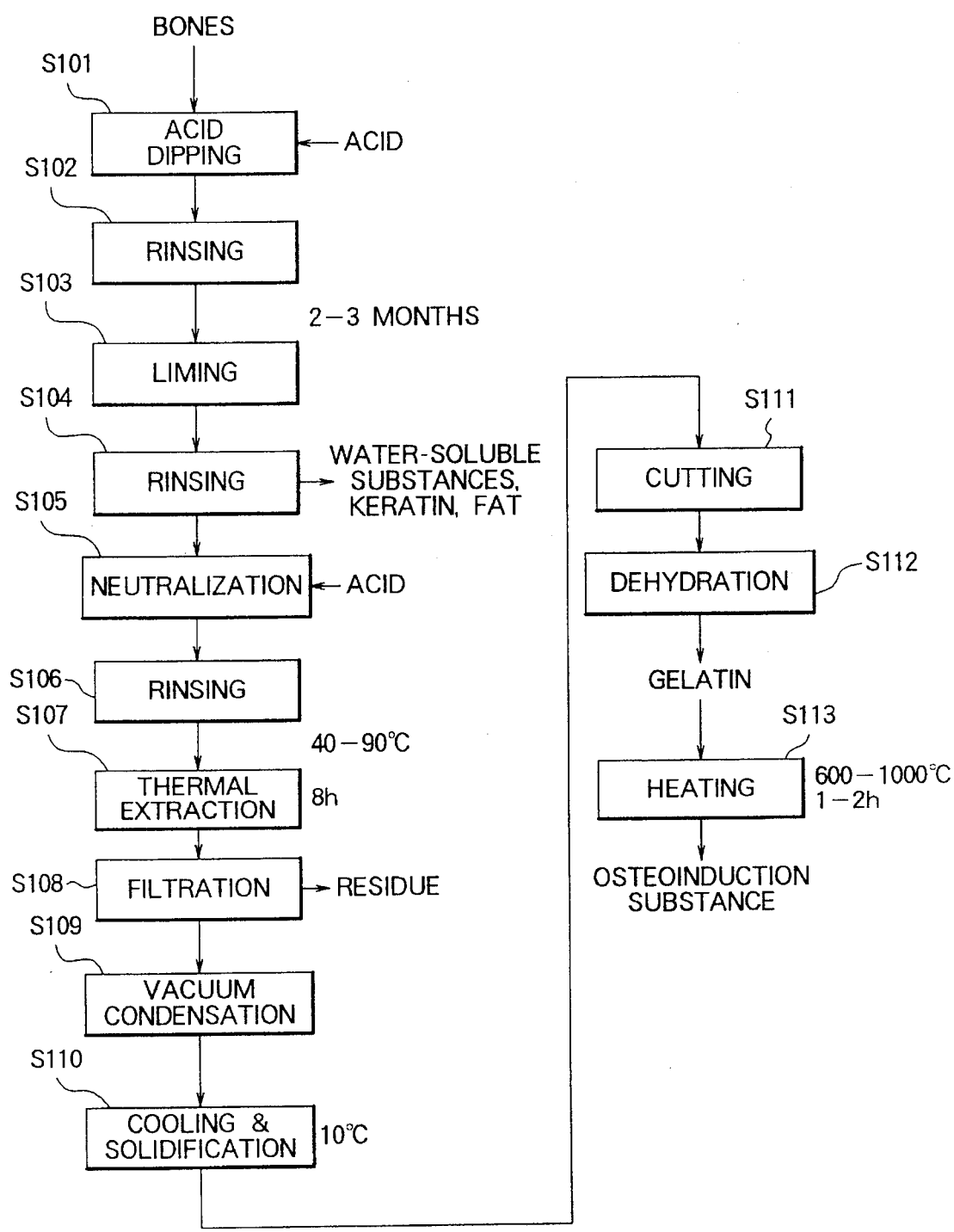
FIG. 1 is a flow chart for describing a conventional method of manufacturing an osteoinduction substance.

FIG. 1 shows a method of manufacturing the osteoinduction substance previously proposed by the present inventor. Referring to FIG. 1, animal bones are dipped in acid such as malic acid or malonic acid in a step S101. In a step S102, the animal bones are rinsed and then left unprocessed for two to three months. Thereafter, in a step S103, the animal bones are subjected to liming. Then, the animal bones are rinsed in a step S104 to remove water-soluble substances, keratin, and fat to obtain a material. In a step S105, the material is neutralized by the use of acid such as malic acid, malonic acid, or hydrochloric acid. In a step S106, the material is rinsed. Subsequently, in a step S107, the material is heated at a temperature between 40° C. and 90° C. for eight hours to obtain an extract. In a step S108, the extract is filtered to collect mother liquor. The mother liquor is subjected to vacuum condensation at a step S109 and cooled at 10° C. in a step S110 to be solidified into a solidified material. The solidified material is cut in a step S111 and dehydrated at 28° C. in a step S112 to obtain gelatin.

Herein, the yield of the gelatin ranges between 10% and 12% when bovine bones are used as the animal bones.

Thereafter, in a step S113, the gelatin is heated at a temperature between 600° C. and 1000° C. for one to two hours to obtain a residue as an osteoinduction substance with a yield of 5 wt % and a pH value of 12.5.

The osteoinduction substance obtained in the method illustrated in FIG. 1 is effective in accelerating creation of a new bone when a small amount of the osteoinduction substance is added to apatite which is known as a bone filling material. When the osteoinduction substance is mixed with chitosan sol, it is possible to prepare a bone filling material of a sheet type because the osteoinduction substance has an ability of gelatinizing the chitosan sol. It has also been confirmed that, by the use of the mixture of the osteoinduction substance and the chitosan sol, the contents of CaO and ZnO can be reduced as compared with a neutral bone filling material of a hardenable type.

To obtain the osteoinduction substance, the gelatin is heated at a temperature between 600° C. and 1000° C. for one to two hours. During this high-temperature process, an offensive odor or malodor is inevitably emitted from the gelatin to bring about environmental pollution. In this connection, the osteoinduction substance must be manufactured by the use of a special heating apparatus capable of dealing with such offensive odor.

As described, the gelatin is heated at such a high temperature ranging between 600° C. and 1000° C. Thus, the conventional method is disadvantageous in view of heat economy.

Now, description will be made as regards embodiments of this invention with reference to the drawing.

Figure 2:
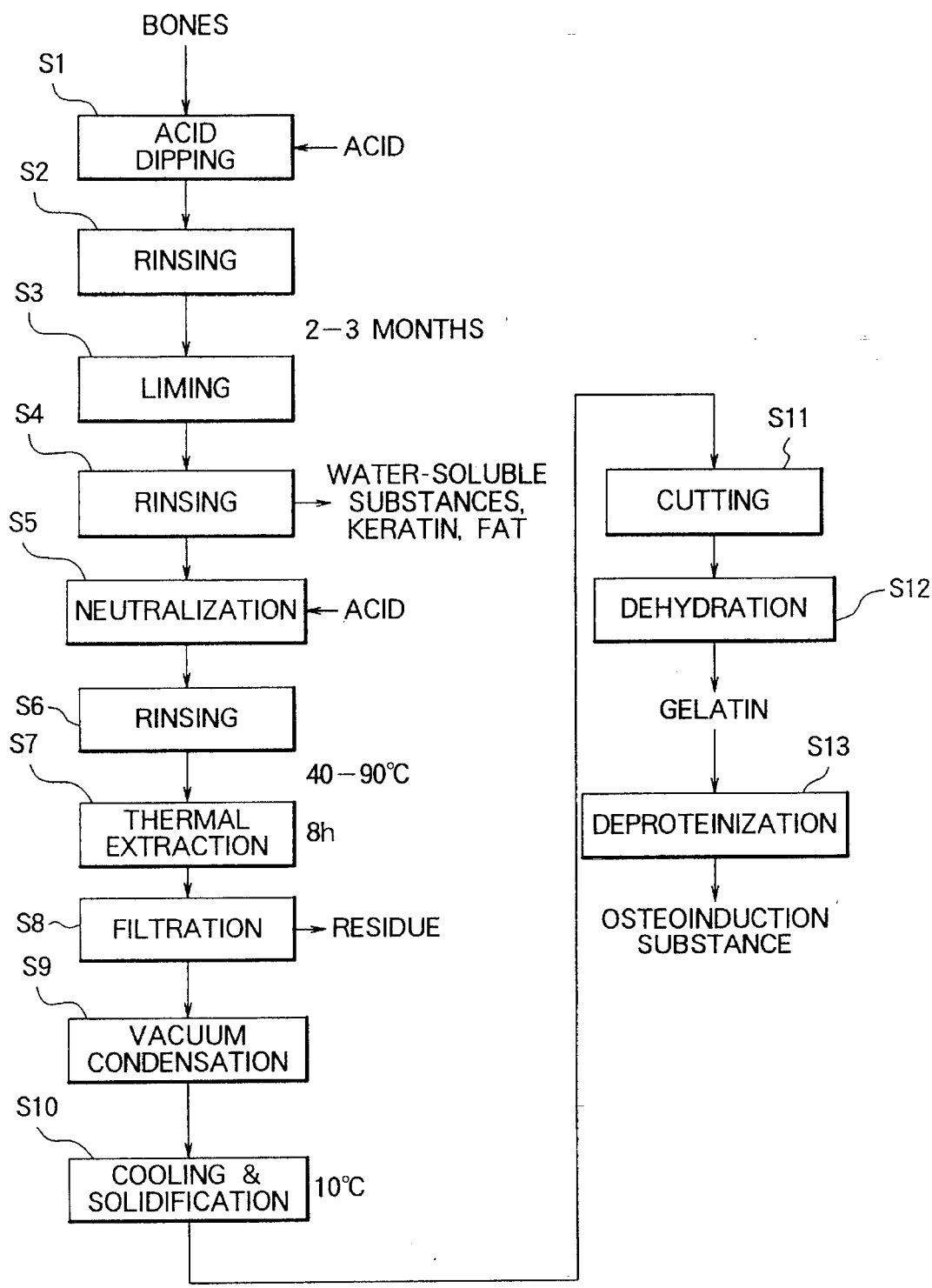
FIG. 2 is a flow chart for describing a method of manufacturing an osteoinduction substance according to an embodiment of this invention.

FIG. 2 shows a method of manufacturing an osteoinduction substance according to an embodiment of this invention. The osteoinduction substance obtained by the method in FIG. 2 is extracted from gelatin by means of nonheat or low-temperature treatment.

Referring to FIG. 2, animal bones are at first dipped in acid such as malic acid or malonic acid in a step S1. In a step S2, the animal bones are rinsed and left unprocessed for two to three months. Thereafter, in a step S3, the animal bones are subjected to liming. Then, the animal bones are rinsed in a step S4 to remove water-soluble substances, keratin, and fat to obtain a starting material. In a step S5, the starting material is neutralized by the use of acid such as malic acid, malonic acid, or hydrochloric acid. In a step S6, the material is rinsed. Subsequently, in a step S7, the material is heated at a temperature between 40° C. and 90° C. for eight hours to obtain an extract.

The extract thus obtained is filtered in a step S8 to collect mother liquor. The mother liquor is subjected to vacuum condensation in a step S9 and cooled at 10° C. in a step S10 to be solidified into a solidified material. The solidified material is cut in a step S11 and dehydrated at 28° C. in a step S12 to obtain the gelatin. Herein, the yield of the gelatin ranges between 10% and 12% when bovine bones are used as the animal bones 1.

Subsequently, in a step S13, the gelatin is dissolved in a nonheat condition by the use of alkaline aqueous solution to deproteinize or remove protein and then is filtered to obtain or extract the osteoinduction substance. As the alkaline aqueous solution, NaOH aqueous solution is herein used.

The above-mentioned step S13 may be modified. Specifically, the gelatin is dissolved in 3–4% NaOH aqueous solution and heated at a low temperature between 80° C. and 85° C. for two to three hours. In this event, it is possible to remove the protein from the gelatin more quickly.

By the use of the above-mentioned technique, it is possible to efficiently extract the osteoinduction substance having an excellent ability of accelerating creation of a bone, without suffering an offensive odor resulting from the high-temperature process. It has been experimentally confirmed that the osteoinduction substance thus extracted contains components similar to those of the conventional osteoinduction substance obtained through the high-temperature heating or firing technique. It has also been confirmed that a bone filling material including the osteoinduction substance contains components similar to those of the conventional bone filling material. The yield of the osteoinduction substance obtained by the above-mentioned technique, namely, a ratio of the amount of the osteoinduction substance to the amount of the gelatin ranged between 5 wt % and 6 wt %.

In order to identify the composition of the osteoinduction substance thus obtained, X-ray diffraction analysis was carried out by the use of an X-ray diffraction analyzer (manufactured by Shimadzu Corporation, XD-D1).

Specifically, a sample of 0.1 g of the osteoinduction substance was thermally decomposed by the use of hydrochloric acid and filtered to obtain a residue. The residue was incinerated, dissolved by alkaline aqueous solution, and then dissolved in hydrochloric acid to obtain test solution. The test solution was adjusted to 50 ml by the use of purified water.

The test solution thus obtained was introduced into the X-ray diffraction analyzer for the X-ray diffraction analysis. As a result of measurement, peaks were observed at the wavelengths of 383.23 nm (corresponding to Mg), 252.61 nm (Si), 180.73 nm (S), 317.93 nm (Ca), and 589.55 nm (Na). Thus, it has been confirmed that the osteoinduction substance contained Mg, Si, S, Ca, and Na.

After the elements were identified as described above, their contents were estimated by an inductively coupled plasma emission spectroscope (manufactured by Shimadzu Corporation, ICPV-1000) for each element with reference to a ratio of peak intensity and background intensity of inductively coupled plasma. The result is shown in Table 1.

TABLE 1

| Element | Estimated Content (wt %) |
|---------|--------------------------|
| Mg      | 8–10                     |
| Si      | 5–8                      |
| S       | 1–3                      |
| Ca      | 60–77                    |
| Na      | 1–2                      |

As a result of the X-ray diffraction analysis, it has been confirmed that Mg, Si, and Ca are present in the form of $MgCO_3$, $Ca_2SiO_4$, CaO, and $Ca(OH)_2$.

It has been revealed that the osteoinduction substance had an ability of gelatinizing chitosan sol. Accordingly, the bone filling material can be formed not only into a hardenable type but also into a sheet type if the osteoinduction substance is mixed with the chitosan sol.

As an example of an application of the osteoinduction substance, description will be made as regards the bone filling material of a sheet type comprising a mixture of the osteoinduction substance and the chitosan sol.

EXAMPLE 1

Chitosan sol was prepared by dissolving 0.5 g of chitosan with 0.5 g of malic acid in 10 cc of the physiological saline solution. 0.02 g of the above-mentioned osteoinduction substance was kneaded into the chitosan sol to form paste. The paste was poured into a vessel to a predetermined thickness and dehydrated by the use of liquid nitrogen to form a sheet. The sheet had a pH value equal to 4.7 and 4.4 when the chitosan sol was prepared by dissolution with the malic acid and the malonic acid, respectively.

Because of such pH values, the sheet could not be straightforwardly used in an organism. It is therefore required to neutralize the sheet to adjust the pH value on the order of 7.0. As a neutralizing agent, malic acid solution or malonic acid solution, alone or in combination, may be used for acidification while alkali substances such as CaOH and MgO, alone or in combination, may be used for alkalization.

The sheet thus obtained has an elastic body such as rubber in a wet condition. At the time of sterilization, the sheet is dehydrated and hardened. Before the sheet is used, the sheet can be restored into the elastic body when immersed in 10 cc of the physiological saline solution for five minutes. Then, the sheet is cut by a cutting tool into a piece having a size corresponding to the dimension of a site in an organic tissue where a new bone is to be created. The piece of the sheet is implanted in the site.

In the meanwhile, in the conventional osteoinduction substance using particulate hydroxyapatite, the particulate hydroxyapatite often migrates to an area between a gingiva and a bone. This may cause inflammation in the gingiva under an occulusal pressure of teeth.

In view of the above, it is desired to use at least one of crystallized and amorphous hydroxyapatite powder having a particle size between 10 and 50 microns. The hydroxyapatite powder may be amorphous in configuration.

Since the osteoinduction substance according to Embodiment 1 has an elastic body, no inflammation is caused in the gingiva. When the sheet is manufactured by the use of liquid nitrogen, a number of gaps are =formed throughout the sheet. This helps the intrusion of new blood vessels into the sheet implanted in the organic tissue. Accordingly, the sheet is quickly grown into a bone to finally complete the creation of the bone.

When the sheet manufactured by the use of the liquid nitrogen was neutralized with the malic acid and CaOH to adjust the pH value to 7.0, the sheet had a hardness of 32 Hs, a tensile strength of 8 $gf/mm^2$, and an elongation of 27%.

EXAMPLE 2

The chitosan sol was prepared by 0.5 g of chitosan, 0.4 g of malonic acid, and 8 cc of physiological saline solution. 0.05 g of the osteoinduction substance and 1.5 g of the hydroxyapatite powder were mixed with the chitosan sol to form a bone filling material of a sheet type which contains the osteoinduction substance and which may be referred to as a bone filling sheet. The sheet had a tensile strength of 12 $gf/mm^2$ and an elongation of 40%.

EXAMPLE 3

The chitosan sol was prepared in the manner similar to Example 2. 0.03 g of the osteoinduction substance and 1.5 g of the hydroxyapatite powder were mixed with the chitosan sol to form the bone filling sheet containing the osteoinduction substance. The sheet had a tensile strength of 10.3 gf/mm² and an elongation of 38%.

EXAMPLE 4

The chitosan sol was prepared in the manner similar to Example 2. 0.02 g of the osteoinduction substance and 1.5 g of the hydroxyapatite powder were mixed with the chitosan sol to form the bone filling sheet containing the osteoinduction substance. The sheet had a tensile strength of 9.7 gf/mm² and an elongation of 32%.

It has been found out that the growth of the bone was accelerated by applying the sheet in any of Examples 1 through 4 to a site of a Jaw bone where a recess was formed.

Next, description will be made as regards a few examples in which the osteoinduction substance is mixed with a bone filling material of a hardenable type.

EXAMPLE 5

The chitosan sol was prepared by dissolving 0.125 g of malic acid and 0.125 g of chitosan in 2 cc of physiological saline solution. 0.02 g of CaO, 0.02 g of ZnO, 0.4 g of hydroxyapatite powder, and 0.02 g of the osteoinduction substance were added to the chitosan sol to obtain the bone filling material. The bone filling material was hardened after lapse of 25 minutes and 29 seconds and had a pH value of 7.7. The bone filling material had a compressive strength of 14 kg/cm² after hardened.

EXAMPLE 6

The chitosan sol was prepared in the manner similar to Example 6. 0.02 g of CaO, 0.03 g of ZnO, 0.4 g of hydroxyapatite powder, and 0.02 g of the osteoinduction substance were added to the chitosan sol to obtain the bone filling material. The bone filling material was hardened after lapse of 7 minutes and had a pH value of 7.9. The bone filling material had a compressive strength of 22 kg/cm² after hardened.

EXAMPLE 7

The chitosan sol was prepared by dissolving 0.1 g of malonic acid and 0.125 g of chitosan in 2 cc of physiological saline solution. 0.01 g of CaO, 0.01 g of ZnO, 0.4 g of hydroxyapatite powder, and 0.03 g of the osteoinduction substance were added to the chitosan sol to obtain the bone filling material. The bone filling material was hardened after lapse of 5 minutes and had a pH value of 7.2. The bone filling material had a compressive strength of 15 kg/cm² after hardened.

It has also been found out that the above-mentioned osteoinduction substance is also effective when it is mixed with at least one of various kinds of apatite. The following description is directed to the case where the osteoinduction substance is mixed with the hydroxyapatite powder.

EXAMPLE 8

As an experimental group of animals, Sprague Dawley female rats of 4 weeks old having a weight of about 110 g were used. Under a shower, a cranial bone of each rat was drilled by a bone drilling bur to form a recess having a diameter of 2 mm and a depth of 0.3 mm. A mixture of 0.5 g of the osteoinduction substance and 5 g of the hydroxyapatite powder was implanted in the recess. On the other hand, the hydroxyapatite powder alone was implanted in a similar recess in another group of rats as a comparative example.

After lapse of two and four weeks, the rats were slaughtered. After decalcification, the implanted sites were stained by hematoxyline-eosin. In the comparative example using the hydroxyapatite powder alone, it was observed that no bone was created in any of the rats in both classes slaughtered after two weeks and four weeks. On the other hand, in the experimental group using the mixture of the osteoinduction substance and the hydroxyapatite powder, Juvenile new bones and, in some rats, matured bones were confirmed in a condition stained red by hematoxyline-eosin in a class slaughtered after two weeks. For another class slaughtered after four weeks, a well-matured bone tissue was confirmed.

Although the bovine bones were used as the animal bones in each example, use may be made of any other animal bones, for example, fish bones.

As described above, the gelatin is processed by the use of the alkaline aqueous solution in a nonheat or a low-temperature condition to obtain the osteoinduction substance. Thus, the osteoinduction substance, the method of manufacturing the bone creation accelerator, and the bone filling material using the osteoinduction substance according to this invention can avoid occurrence of an offensive odor and is advantageous in heat economy. This is because a high-temperature heat treatment is not required at all.

As will be clearly understood from the above-mentioned experimental results, the osteoinduction substance is effective in creation of the new bone when a small amount of the osteoinduction substance is added to the hydroxyapatite powder. When the osteoinduction substance is mixed with at least one of the hydroxyapatite powder and the chitosan, the bone filling material is obtained.

Since the osteoinduction substance derived from the gelatin has an ability of gelatinizing the chitosan sol, it is possible to form the bone filling material of a sheet type by mixing the osteoinduction substance and the chitosan sol. It has been confirmed that, by the use of the mixture of the osteoinduction substance and the chitosan sol, the contents of CaO and ZnO can be reduced as compared with the conventional bone filling material of a hardenable type.

What is claimed is:

1. An osteoinduction substance which contains Mg, Si, Ca, and Na and which is prepared by the steps of subjecting animal bones to liming, neutralization, thermal extraction, condensation, and dehydration to obtain gelatin; and subjecting said gelatin to deproteinization which is carried out through a nonheat process or a low-temperature process.

2. An osteoinduction substance as claimed in claim 1, wherein said deprotenization is carried out by dissolving said gelatin in alkaline aqueous solution.

3. An osteoinduction substance as claimed in claim 2, wherein NaOH aqueous solution is used as said alkaline aqueous solution.

4. A method of manufacturing an osteoinduction substance, comprising the steps of subjecting animal bones to acid dipping, liming, neutralization, thermal extraction, condensation, and dehydration to obtain gelatin; subjecting said gelatin to deproteinization which is carried out through a nonheat process or a low-temperature process; and filtering said solution to extract said osteoinduction substance.

5. A method of manufacturing an osteoinduction substance as claimed in claim 4, wherein said deproteinization is carried out by dissolving said gelatin in alkaline aqueous solution.

6. A method of manufacturing an osteoinduction substance as claimed in claim 5, wherein NaOH aqueous solution is used as said alkaline aqueous solution.

7. A method of manufacturing an osteoinduction substance as claimed in claim 6, wherein said NaOH aqueous solution is heated during said deproteinization at a low temperature between 80° C. and 85° C. for two to three hours.

8. A bone filling material comprising a mixture of an osteoinduction substance and at least one of hydroxyapatite powder and chitosan, said osteoinduction substance containing Mg, Si, Ca, and Na and manufactured by the steps of subjecting animal bones to liming, neutralization, thermal extraction, condensation, and dehydration to obtain gelatin, and subjecting said gelatin to deproteinization which is carried out through a nonheat process or a low,temperature process.

9. A bone filling material as claimed in claim 8, wherein said deproteinization is carried out by dissolving said gelatin in,alkaline aqueous solution.

10. A bone filling material as claimed in claim 9, wherein NaOH aqueous solution is used as said alkaline aqueous solution.

11. A bone filling material as claimed in claim 8, said material including chitosan sol which is gelatinized by said osteoinduction substance to form said bone filling material into a sheet.

12. A bone filling material as claimed in claim 8, wherein said hydroxyapatite powder has a particle size between 10 and 50 microns and includes at least one of crystallized hydroxyapatite powder and amorphous hydroxyapatite powder.

13. A bone filling material as claimed in claim 8, wherein said hydroxyapatite powder is composed of amorphous hydroxyapatite powder.

14. A method of manufacturing a bone filling material, comprising the steps of:

preparing an osteoinduction substance by subjecting animal bones to acid dipping, liming, neutralization, thermal extraction, condensation, and dehydration to obtain gelatin, subjecting said gelatin to deproteinization which is carried out through a nonheat process or a low-temperature process, and filtering said solution to obtain said osteoinduction substance; and mixing said osteoinduction substance with at least one of hydroxyapatite powder and chitosan.

15. A method of manufacturing a bone filling material as claimed in claim 14, comprising the steps of dissolving hydroxyapatite powder and chitosan by acid using physiological saline solution to form a sol material; and kneading said osteoinduction substance into said sol material to form paste as said bone filling material.

16. A method of manufacturing a bone filling material as claimed in claim 15, said method further comprising the steps of dehydrating said paste by the use of liquid nitrogen, and shaping said paste into a sheet which serves as said bone filling material.

17. A method of manufacturing a bone filling material as claimed in claim 14, wherein said deproteinization is carried out by dissolving said gelatin in alkaline aqueous solution.

18. A method of manufacturing a bone filling material as claimed in claim 17, wherein NaOH aqueous solution is used as said alkaline aqueous solution.

19. A method of manufacturing a bone filling material as claimed in claim 18, wherein said NaOH aqueous solution is heated during said deproteinization at a low temperature between 80° C. and 85° C. for two to three hours.

* * * * *